United States Patent
Sugahara et al.

(10) Patent No.: US 9,402,298 B2
(45) Date of Patent: Jul. 26, 2016

(54) METHOD OF MANUFACTURING RADIO FREQUENCY ACCELERATOR, RADIO FREQUENCY ACCELERATOR, AND CIRCULAR ACCELERATOR SYSTEM

(71) Applicants: Kengo Sugahara, Tokyo (JP); Kazushi Hanakawa, Tokyo (JP); Yasuto Kishii, Tokyo (JP); Kazuo Yamamoto, Tokyo (JP)

(72) Inventors: Kengo Sugahara, Tokyo (JP); Kazushi Hanakawa, Tokyo (JP); Yasuto Kishii, Tokyo (JP); Kazuo Yamamoto, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/653,012

(22) PCT Filed: Feb. 28, 2013

(86) PCT No.: PCT/JP2013/055407
§ 371 (c)(1),
(2) Date: Jun. 17, 2015

(87) PCT Pub. No.: WO2014/132391
PCT Pub. Date: Sep. 4, 2014

(65) Prior Publication Data
US 2016/0014877 A1  Jan. 14, 2016

(51) Int. Cl.
| | | |
|---|---|---|
| H05H 7/08 | (2006.01) |
| H05H 7/02 | (2006.01) |
| H05H 7/22 | (2006.01) |
| H05H 9/04 | (2006.01) |
| H05H 13/04 | (2006.01) |
| A61N 5/10 | (2006.01) |
| H01J 9/42 | (2006.01) |
| H01J 9/44 | (2006.01) |

(52) U.S. Cl.
CPC .. *H05H 7/08* (2013.01); *A61N 5/10* (2013.01); *H01J 9/42* (2013.01); *H01J 9/44* (2013.01);
(Continued)

(58) Field of Classification Search
CPC ............. H05H 7/08; H05H 7/02; H05H 7/22; H05H 9/041; H05H 9/045; H05H 9/057; H05H 13/04; A61N 5/10; H01J 9/42; H01J 9/44
USPC ........................................................ 315/503
See application file for complete search history.

(56) References Cited

U.S. PATENT DOCUMENTS

| | | | | |
|---|---|---|---|---|
| 6,777,893 B1 * | 8/2004 | Swenson | ................... | H05H 7/22 315/505 |
| 8,736,198 B2 * | 5/2014 | Haruna | ..................... | H05H 7/02 250/251 |

(Continued)

FOREIGN PATENT DOCUMENTS

| | | |
|---|---|---|
| JP | 3-034252 A | 2/1991 |
| JP | 5-258898 A | 10/1993 |

(Continued)

OTHER PUBLICATIONS

International Search Report (PCT/ISA/210) mailed on May 28, 2013, by the Japanese Patent Office as the International Searching Authority for International Application No. PCT/JP2013/055407.

*Primary Examiner* — Dylan White
(74) *Attorney, Agent, or Firm* — Buchanan Ingersoll & Rooney PC

(57) ABSTRACT

A method of manufacturing a radio frequency accelerator that accelerates charged particles injected into a second-stage linear accelerator from a first-stage linear accelerator includes a step of setting a value of a power distribution factor R for the power distributor to supply radio frequency power to the second-stage linear accelerator and a value of a ratio $L/\omega$ of a length L of the matching section between the outlet of the first-stage linear accelerator and the inlet of the second-stage linear accelerator to the angular frequency $\omega$ of the radio frequency power, so that a charged particle beam is extracted from the second-stage linear accelerator over a range of the total radio frequency power wider than a widest allowable range among allowable total radio frequency power ranges determined for each phase of charged particles on the basis of phase acceptance of the second-stage accelerator.

12 Claims, 12 Drawing Sheets

(52) U.S. Cl.
CPC . *H05H 7/02* (2013.01); *H05H 7/22* (2013.01); *H05H 9/041* (2013.01); *H05H 9/045* (2013.01); *H05H 9/047* (2013.01); *H05H 13/04* (2013.01); *H05H 2007/025* (2013.01); *H05H 2007/082* (2013.01); *H05H 2007/227* (2013.01)

(56) References Cited

U.S. PATENT DOCUMENTS 8,742,699 B2 * 6/2014 Umezawa .............. G21K 1/093
 315/500
2003/0048080 A1 * 3/2003 Amemiya ................ G21K 5/04
 315/500
2005/0231138 A1 * 10/2005 Nakanishi ................ G21K 5/04
 315/500

FOREIGN PATENT DOCUMENTS

| JP | 5-290997 A | 11/1993 | |
|---|---|---|---|
| JP | 7-057898 A | 3/1995 | |
| JP | 2010-027529 A | 2/2010 | |
| JP | EP 2384099 A2 * | 11/2011 | ............. G21K 1/093 |

* cited by examiner

SOLID LINE : PHASE DISTRIBUTION OF CHARGED PARTICLES EXTRACTED
  FROM FIRST-STAGE LINEAR ACCELERATOR
BROKEN LINE : PHASE ACCEPTANCE OF SECOND-STAGE LINEAR ACCELERATOR

SOLID LINE : PHASE DISTRIBUTION OF CHARGED PARTICLES EXTRACTED
FROM FIRST-STAGE LINEAR ACCELERATOR
BROKEN LINE : PHASE ACCEPTANCE OF SECOND-STAGE LINEAR ACCELERATOR

METHOD OF MANUFACTURING RADIO FREQUENCY ACCELERATOR, RADIO FREQUENCY ACCELERATOR, AND CIRCULAR ACCELERATOR SYSTEM

TECHNICAL FIELD

The present invention relates to radio frequency accelerators for generating a particle beam for a particle beam therapy system or the like performing therapy by irradiating a diseased portion such as of a tumor with the particle beam, and more particularly to a radio frequency accelerator used as an injector for injecting a particle beam into a circular accelerator such as a synchrotron.

BACKGROUND ART

In particle beam cancer therapy systems, an injector is used as a pre-stage accelerator for injecting a particle beam into a circular accelerator. A linear accelerator is used as the injector in many cases. In ion beams, interaction (electric repulsive force) between individual particles (ions) in the ion beams is referred to as space-charge effect. Since the repulsive force is mitigated with increasing energy, acceleration is required as much as possible in the pre-stage of injection into the circular accelerator.

As for protons, for example, it has been known that a linear accelerator suitable for accelerating a beam from an ion source and a linear accelerator manufacturable in a relatively compact size as two stage acceleration are different in structure. In applications other than particle beam cancer therapy systems, connecting of multiple-type linear accelerators in series has been also employed for acceleration up to a relatively high energy level.

Ordinarily, in a case of supplying radio frequency waves to an accelerator (a radio frequency accelerator) having two radio frequency cavities, the radio frequency waves supplied to each radio frequency cavity need to be synchronized with respect to the beam. For that reason, it is necessary to input the radio frequency waves having the same frequency and synchronized phases into each radio frequency cavity. Furthermore, the radio frequency power input into each radio frequency cavity and the respective phases of the radio frequency waves input into the two radio frequency cavities are designed and adjusted for the beam to have good quality and high transmission efficiency (see Patent Document 1 for example).

A radio frequency wave of high power needs to be supplied to the radio frequency accelerator. High-power radio frequency generators are expensive and made using vacuum tubes in many cases. This involves replacement of the tubes, raising a problem of increasing maintenance costs. For that reason, using a power distributor for supplying power to the two radio frequency cavities brings about merits of low costs and reliability improvement because of reduction in the amount of power generators (see Patent Document 2 for example).

However, generation of the high radio frequency power by one power generator and distribution of the radio frequency power by a resonant-coupler-type power distributor cannot adjust independently the respective phases of the radio frequency power to be supplied to the cavities because of a problem due to the principle of the power distributor. Moreover, it has been relatively difficult to adjust the power to each cavity for the beam to have good quality and high transmission efficiency.

PRIOR ART DOCUMENT

Patent Document
  Patent Document 1: JP H03-034252 A
  Patent Document 2: JP 2010-027529 A

SUMMARY OF THE INVENTION

Problem that the Invention is to Solve

In the case of accelerating charged particles by arranging two radio frequency accelerators of different types in series as described above, it has been conventionally considered that the charged particles can be accelerated only in narrow bounds around design values of power and phases of the radio frequency waves by optimally adjusting the respective power and phases of radio frequency waves applied to the two radio frequency accelerators.

However, the present inventors elucidate energy and phase behavior of the charged particles to the input radio frequency power and found out that there exists a condition that allows for acceleration of the charged particles even over a wider range of the radio frequency power.

The present application aims at providing a radio frequency accelerator that have two linear accelerators, a first-stage linear accelerator and a second-stage linear accelerator, arranged in series and coupled with each other by a power distributor, and ensures matching between the first-stage accelerator and the second-stage accelerator even when radio frequency power applied is varied, and is easy to adjust the power.

Means for Solving the Problem

In a radio frequency accelerator that includes a first-stage linear accelerator for accelerating charged particles injected into the first-stage linear accelerator from an ion source; a second-stage linear accelerator for accelerating a charged particle beam injected into the second-stage linear accelerator from the first-stage linear accelerator through a matching section; a radio frequency power source for generating total radio frequency power to be supplied to the first-stage linear accelerator and the second-stage linear accelerator; and a power distributor for distributively supplying the total radio frequency power supplied from the radio frequency power source to the first-stage linear accelerator and the second-stage linear accelerator, a manufacturing method according to the present invention for the radio frequency accelerator includes a step of setting a value of a power distribution factor R for the power distributor to supply the radio frequency power to the second-stage linear accelerator and a value of a ratio L/ω of a length L of the matching section between an outlet of the first-stage linear accelerator and an inlet of the second-stage linear accelerator to an angular frequency ω of the radio frequency power, so that the charged particle beam is extracted from the second-stage linear accelerator over a range of the total radio frequency power wider than a widest allowable range among allowable total radio frequency power ranges determined for each phase of charged particles on the basis of phase acceptance of the second-stage accelerator.

Advantages of the Invention

Since a value of the power distribution factor R for the power distributor to supply radio frequency power to the second-stage linear accelerator and a value of the ratio L/ω of the matching section length L between the outlet of the first-stage linear accelerator and the inlet of the second-stage linear accelerator to the angular frequency ω of the radio frequency power is set so that the charged particle beam is extracted from the second-stage linear accelerator over a wide range of the total radio frequency power $P_{rf,total}$ generated by a radio frequency power generator, a radio frequency accelerator can be provided that ensures matching between the first-stage accelerator and the second-stage accelerator even when the supplied radio frequency power is varied, and is easy to adjust the power. As a result, further employing the radio frequency accelerator as an injector for a circular accelerator brings about an effect of providing a radio frequency accelerator that is capable of generating by adjusting the radio frequency power a preferable characteristic for a charged particle beam to be injected into the circular accelerator.

EMBODIMENTS FOR CARRYING OUT THE INVENTION

Embodiment 1

Figure 1:
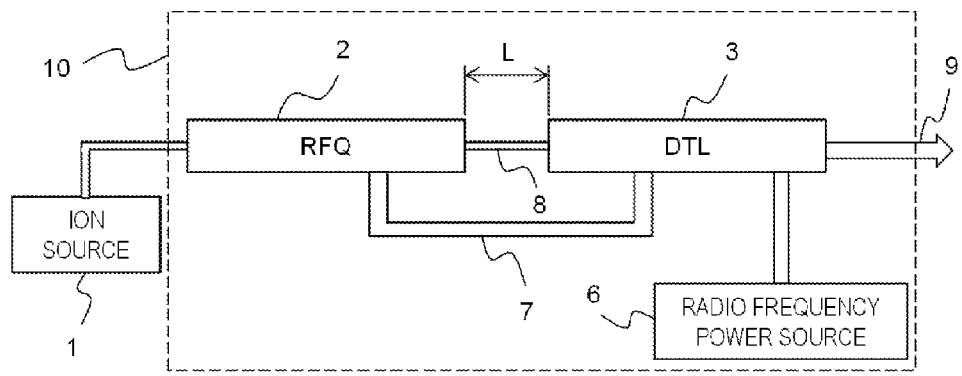
FIG. 1 is a block diagram showing a schematic configuration of a radio frequency accelerator according to Embodiment 1 of the present invention.

FIG. 1 is a block diagram showing a schematic configuration of a radio frequency accelerator 10 according to Embodiment 1 of the present invention. Ions (charged particles) generated in an ion source 1 are injected into a first-stage linear accelerator 2 included in the radio frequency accelerator 10. The charged particles accelerated by the first-stage linear accelerator 2 are injected into a second-stage linear accelerator 3 thereby to be further accelerated. A charged particle beam extracted from the second-stage linear accelerator 3 is a charged particle beam 9 extracted from the radio frequency accelerator 10 according to Embodiment 1 of the present invention. Hereinafter, descriptions are made by taking a radio frequency quadrupole (RFQ) linac as an example of the first-stage linear accelerator 2 and an alternating phase focused interdigital H-mode drift-tube linac (APF-IH DTL) as an example of the second-stage linear accelerator 3. Note that the first-stage accelerator is not limited to a RFQ type but may be a radio frequency focused interdigital (RFI) type. And the second-stage accelerator is not limited to an APF type but may be an ordinary DTL.

In the radio frequency accelerator 10, a radio frequency wave for accelerating the charged particles is generated and supplied to the second-stage linear accelerator 3, an APF-IH DTL, by a radio frequency power source 6. Radio frequency wave supplied to the first-stage linear accelerator 2, a RFQ linac, is distributed using high frequency coupling with the second-stage linear accelerator 3 by a power distributor 7 called "resonant coupler" (resonant-coupler-type power distributor).

There is provided a matching section 8 as a part for adjusting the phase and a beam profile in the transverse direction (the longitudinal direction is the beam traveling direction) so that the charged particles to be injected into the second-stage linear accelerator 3 from the first-stage linear accelerator 2 has a phase suitable for acceleration by the second-stage linear accelerator 3, the APF-IH DTL.

A radio frequency accelerator for charged particles is configured to supply radio frequency power to a radio frequency cavity to accelerate the charged particles by an electrical field produced in the radio frequency cavity. Supplying radio frequency power to the radio frequency cavity induces a radio frequency field as a standing wave. Since the radio frequency field alternates between positive and negative in response to its phase, the electric field is designed to be induced in synchronism with the acceleration of the charged particles. The charged particles cannot be accelerated to a high energy level without an optimal design by computer because the charged particles repeat acceleration and deceleration by being subject to the alternating positive and negative electric field. There are several types of accelerators such as a RFQ linac, a DTL, and a RFI linac depending on difference in the design principle of the electric field. Operational characteristics of a RFQ linac, an APF-IH DTL, and a resonant-coupler-type power distributor are described below.

(1) Radio Frequency Quadrupole (RFQ) Linac

A RFQ linac performs a first-stage acceleration by radio-frequency bunching an ion beam generated by the ion source. Electrode pairs called vanes are arranged oppositely to generate a radio frequency quadrupole electric field. On the tips of the vanes, a wavy structure called modulation is formed. Charged particles are accelerated by synchronizing their velocity with the phase of the radio frequency waves. Cavities are formed outside the vanes to resonate at a certain frequency. The RFQ linac is an accelerator suitable for accelerating charged particles that are out of phase and have a low energy level of about 50 keV up to an energy level of the order of MeV. This is the reason why the RFQ linac is suitable as the first-stage accelerator for acceleration of directly injected charged particles generated by the ion source.

(2) Alternating Phase Focused Interdigital H-Mode Drift Tube Linac (APF-IH DTL)

An IH DTL has a structure such that hollow cylindrical conductors called "drift tube" are vertically supported alternately to plates called ridges each disposed in the accelerating direction of the beam axis at the top and the bottom of the resonant cavity inside. The APF is a focusing method for performing acceleration of and focusing of ions at the same time by a radio frequency electric field generated inside the resonant cavity. The method completely eliminates a focusing element such as a quadrupole electromagnet necessary for a conventional linear accelerator to focus a beam, thus allowing miniaturization of the IH DTL. However, the accelerator of this type, since it utilizes an electric field for focusing as well as acceleration, is very sensitive to the inlet beam energy and the inlet beam phase. Accordingly, charged particles having an energy level and a phase apart from a design values cannot be accelerated even if they are injected into the accelerator.

(3) Resonant-Coupler-Type Power Distributor

A resonant-coupler-type power distributor is configured with coaxial tubes and a plurality of accelerating cavities connected therethrough, and utilizes a technology of operating three cavities as coupled cavities to resonate by optimally designing the length of the coaxial tube. While a large amount of radio frequency power is input into the acceleration cavities at both ends by operating the three cavities in the π/2 mode, no radio frequency power is input into the resonant-coupler-type power distributor itself. Distribution of the radio frequency power is adjusted by varying the lengths or the like of the coaxial tube having a stub structure or the like attached to the resonant-coupler-type power distributor. If operated not in the π/2 mode, the radio frequency power is also input into the resonant-coupler-type power distributor itself, causing electric discharge or the like. When operated in the π/2 mode, radio frequency wave whose phase difference between both cavities is fixed to exact 180 degrees is supplied to both end cavities.

Conventionally, radio frequency power has been separately supplied to two different accelerators from two radio frequency power sources. In a case of using the two radio frequency power sources, since the phases are adjusted such as by control, the phases are affected by control instabilities such as due to temperature and disturbances. In a case of using the resonant-coupler-type power distributor, on the other hand, instabilities due to such disturbing factors are eliminated; however, a value of the phase set in the initial installation stage cannot be adjusted. Moreover, since alteration of the power distribution factor needs change of the length or the like of the coaxial tube having a stub structure or the like attached to the resonant-coupler-type power distributor and is not as easy as the power input from the power source is altered on the setting panel, the adjustment in the initial installation stage has been relatively difficult.

Next, descriptions are made of characteristics of the charged particle beams extracted from each accelerator, a characteristic required for the charged particle beam to be injected into the second-stage accelerator 3 that is the APF-IH DTL, and the like. In particular, the process of finding out the configuration of the present invention will be described with elucidation of energy and phase behavior of the charged particle beam to the radio frequency power.

Figure 2:
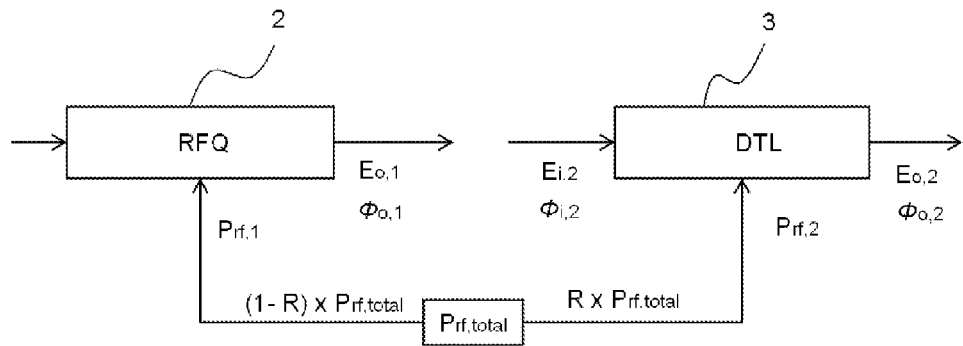
FIG. 2 is a conceptual diagram for explaining symbol expressions of parameters used in the present application.

For the description, symbol expressions of parameters are defined here. The center energy of the energy distribution and the center phase of the phase distribution of the charged particles contained in the charged particle beam are expressed by E and $\phi$, respectively. Suffixes "i" and "o" are added to parameters concerning the inlet and outlet of the accelerators, and suffixes "1" and "2" are added to parameters concerning the first-stage linear accelerator 2 and the second-stage linear accelerator 3, respectively. For example, the center energy and the center phase of the charged particle beam at the outlet of the first-stage linear accelerator 2 are expressed as $E_{o,1}$ and $\phi_{o,1}$, and the radio frequency power supplied to the first-stage linear accelerator 2 and that supplied to the second-stage linear accelerator 3 are expressed as $P_{rf,1}$ and $P_{rf,2}$, respectively. These expressions are shown in FIG. 2.

The sum $P_{rf,1}+P_{rf,2}$ of the radio frequency power supplied to both accelerators is total radio frequency power $P_{rf,total}$ supplied plied from the radio frequency power source 6. Here, a power distribution factor R for the radio frequency power distributed to the second-stage linear accelerator 3 by means of the resonant-coupler-type power distributor 7 is defined by the following equations:

$$P_{rf,2}=R*P_{rf,total} \text{ and}$$

$$P_{rf,1}=(1-R)*P_{rf,total}.$$

In the radio frequency accelerator of the present invention, the charged particles extracted from the first-stage linear accelerator 2, a RFQ linac, are injected into the second-stage linear accelerator 3, an APF-IH DTL, through the matching section 8. The charged particles extracted from the first-stage linear accelerator 2 collect around the position of the center value of the phase in the traveling direction to become beam-shaped bunches. Such bunches of the beam are called "bunched beam". Among the charged particles in the charged particle beam injected into the second-stage linear accelerator 3, only charged particles around the center energy and the center phase suitable for acceleration in the second-stage linear accelerator 3 are accelerated. The center energy and the center phase have certain values suitable for accelerating the charged particles to be injected into the second-stage linear accelerator 3 and there are allowable bounds around the values. Only particles within the allowable bounds are accelerated. Accordingly, when the center values of energy and phase of the injected charged particles are out of the bounds, no acceleration occurs at all in the second-stage linear accelerator 3. Furthermore, when the energy and phase of the injected charged particles broadly spread beyond the allowable bounds, the transmission efficiency decreases even though their center values do not deviate from the bounds.

The allowable bounds are referred to as acceptance in the field of accelerators. Here, acceptance for the energy is referred to as energy acceptance, and that for the phase is referred to as phase acceptance. These center energy, center phase, energy acceptance, and phase acceptance suitable for acceleration can be calculated by an analysis using a computer.

Figure 3:
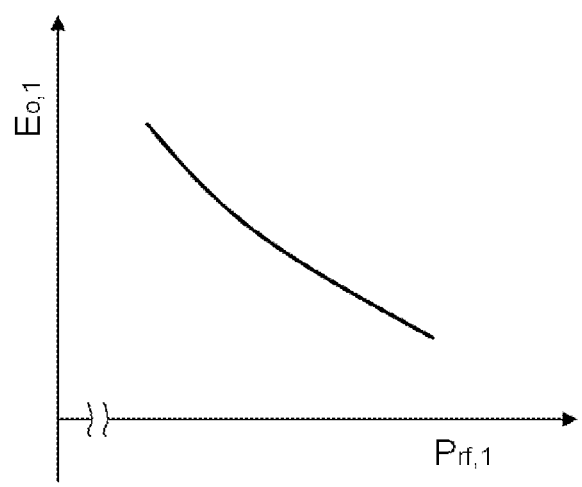
FIG. 3 is a graph showing an example of an energy characteristic of a charged particle beam extracted from a first-stage linear accelerator of the radio frequency accelerator according to the present invention.
Figure 4:
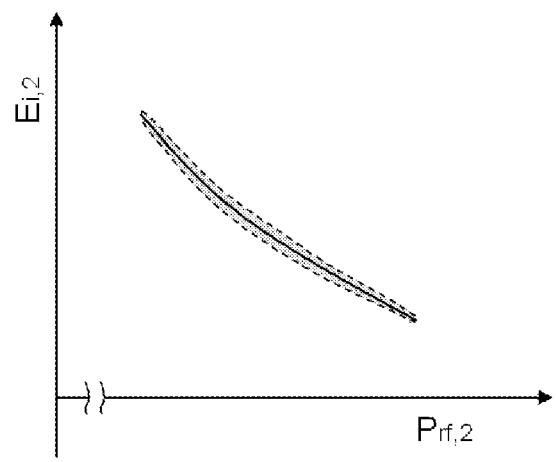
FIG. 4 is a graph showing an example of a designed energy characteristic required for a charged particle beam to be injected into a second-stage linear accelerator of the radio frequency accelerator according to the present invention.

First, the energy of the charged particle beam is considered. Since the matching section 8 has ordinarily no parts of generating an electric field and magnetic fields do no work, there is no change in energy. Hence, the energy of the charged particles does not change while passing through the matching section 8. Therefore, the energy of the charged particles extracted from the first-stage linear accelerator 2 is the energy of the charged particles to be injected into the second-stage linear accelerator 3. FIG. 3 shows variation of the center energy $E_{o,1}$ of the charged particle beam extracted from the first-stage linear accelerator 2 with respect to the radio frequency power $P_{rf,1}$ supplied to the first-stage linear accelerator 2. The first-stage linear accelerator 2 can accelerates the charged particles in a certain range of the radio frequency power $P_{rf,1}$. The energy $E_{o,1}$ has a characteristic that it decreases as $P_{rf,1}$ increases in this range. FIG. 4 shows variation of the inlet center energy $E_{i,2}$ of the charged particle beam suitable for acceleration in the second-stage linear accelerator 3, the APF-IH DTL, with respect to the radio frequency power $P_{rf,2}$ supplied to the second-stage linear accelerator 3. The energy $E_{i,2}$ suitable for acceleration has a characteristic that it decreases as $P_{rf,2}$ increases. In FIG. 4, the center energy is expressed by the solid line and the limit of above-described energy acceptance is expressed by the two broken lines. Charged particles whose energy is out of the energy acceptance are not accelerated at all.

In the configuration of the radio frequency accelerator according to Embodiment 1 of the present invention, since the radio frequency power input to the first-stage linear accelerator 2 and the second-stage linear accelerator 3 is distributively supplied by the resonant-coupler-type power distributor 7, the variation rate of the radio frequency power supplied to both accelerators is constant. Increase of the output of the radio frequency power source 6 decreases the energy $E_{o,1}$ of the charged particles extracted from the first-stage linear accelerator 2 and also decreases the energy $E_{i,2}$ suitable for accelerating the charged particles to be injected into the second-stage linear accelerator 3. Hence, an appropriate design makes it possible to implement an accelerator that is capable of matching energy even when the radio frequency power is varied.

Figure 5:
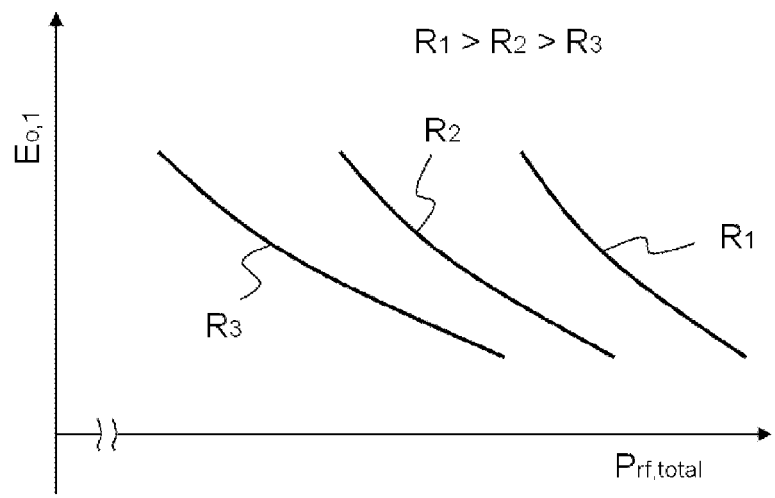
FIG. 5 is a graph showing an example of energy characteristics of the charged particle beam extracted from the first-stage linear accelerator of the radio frequency accelerator according to the present invention, with power distribution factors being taken as parameters.
Figure 6:
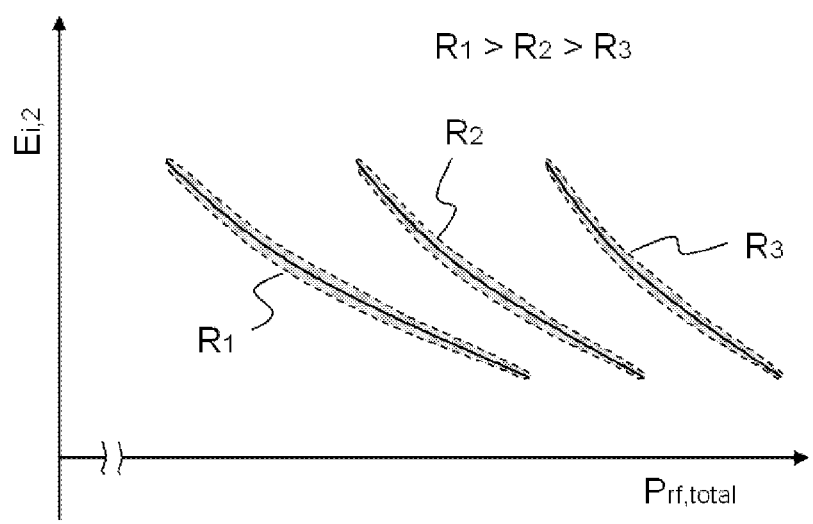
FIG. 6 is a graph showing an example of a design-value example of energy characteristics required for the charged particle beam to be injected into the second-stage linear accelerator of the radio frequency accelerator according to Embodiment 1 of the present invention, with power distribution factors being taken as parameters.

FIGS. 5 and 6 are graphs showing characteristics by changing the horizontal axes of FIGS. 3 and 4 to the output $P_{rf,total}$ of the radio frequency power source 6, with values of the power distribution factor R for the radio frequency power distributed to the second-stage linear accelerator 3 being taken as parameters. Since radio frequency power $P_{rf,2}$ distributed to the second-stage linear accelerator 3 is $R*P_{rf,total}$, relatively smaller radio frequency power $P_{rf,total}$ is suitable for acceleration when R is larger. Conversely, when R is smaller, relatively larger radio frequency power $P_{rf,total}$ is suitable for acceleration. Thus, characteristics of energy $E_{i,2}$ suitable for accelerating the charged particle beam to be injected into the second-stage linear accelerator 3 are as shown in FIG. 6, with values of R having the relationship of $R_1>R_2>R_3$ being taken as parameters. In FIG. 6, the solid lines indicate the center energy suitable for acceleration and the pairs of broken lines indicate the limits of energy acceptance. That is, FIG. 6 shows that charged particles having energy within the bounds between a pair of broken lines can be accelerated in the case of a certain value of R. On the other hand, since the radio frequency power distributed to the first-stage linear accelerator 2 is $(1-R)*P_{rf,total}$, relatively larger radio frequency power $P_{rf,total}$ is suitable for acceleration when R is larger. Conversely, when R is smaller, relatively smaller radio frequency power $P_{rf,total}$ is suitable for acceleration. Thus, characteristics of energy suitable for accelerating the charged particle beam extracted from the first-stage linear accelerator 2 are shown as FIG. 5, with the same $R_1$, $R_2$, and $R_3$ as above being taken as parameters.

The characteristic in the case of the power distribution factor being $R_2$ among the variation characteristics of $E_{o,1}$ shown in FIG. 5 matches with the energy acceptance characteristic in the case of the power distribution factor being $R_2$ among the variation characteristics of $E_{i,2}$ shown in FIG. 6. By setting the power distribution factor of the resonant-coupler-type power distributor 7 to $R_2$, the charged particle beam extracted from the first-stage linear accelerator 2 has a value of the energy $E_{i,2}$ suitable for the charged particles to be injected into the second-stage linear accelerator 3 to be accelerated over the wide output range of the radio frequency power source 6. As described above, it is found that there exists a value of the power distribution factor R that matches an extraction energy characteristic, which is a characteristic of the energy $E_{o,1}$ of the charged particles extracted from the first-stage linear accelerator 2 with respect to variation of the radio frequency power, with an energy acceptance characteristic, which is a characteristic of the energy $E_{i,2}$ with respect to variation of the radio frequency power, suitable for accelerating the charged particles to be injected into the second-stage linear accelerator 3.

Figure 7:
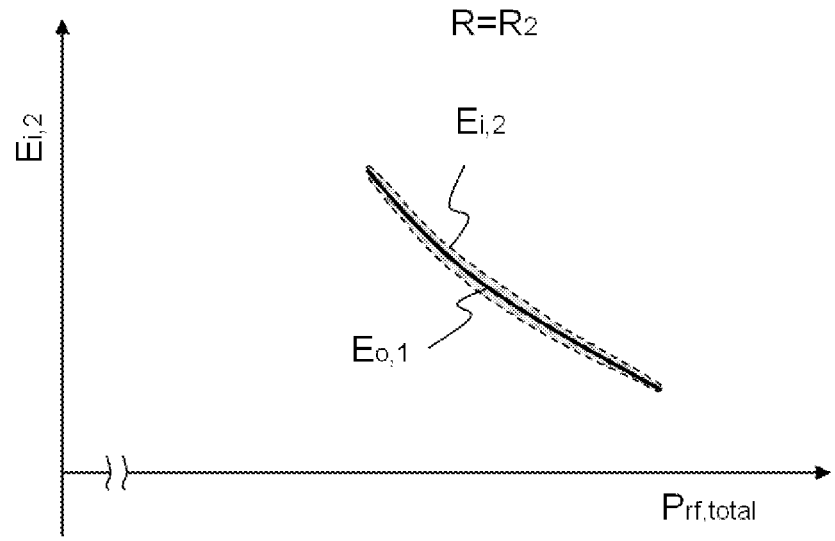
FIG. 7 is a graph showing matching between an energy characteristic of the charged particle beam extracted from the first-stage linear accelerator of the radio frequency accelerator and an energy characteristic required for the charged particle beam to be injected into the second-stage linear accelerator, in the radio frequency accelerator according to Embodiment 1 of the present invention.

Here, an explanation is made to what extent both characteristics described above need to be matched with each other. For a certain value of R, it is difficult to exactly match the characteristic curve of $E_{o,1}(P_{rf,total})$ shown in FIG. 5 with the characteristic curve, i.e., the center energy within the energy acceptance shown in FIG. 6. When the center energy $E_{o,1}(P_{rf,total})$ of the charged particle beam extracted from the first-stage linear accelerator 2 is within the energy acceptance shown in FIG. 6, all charged particles extracted from the first-stage linear accelerator 2 or part of them, even if the transmission efficiency decreases, are accelerated by the second-stage linear accelerator 3. Such a matching condition is schematically illustrated in FIG. 7. In a case of the extraction energy characteristic curve $E_{o,1}(P_{rf,total})$ in the case of $R_2$ shown in FIG. 5 being within the bounds of the energy acceptance in the case of $R_2$ shown in FIG. 6, the relationship between the curve and the range is as shown in FIG. 7.

Figure 8:
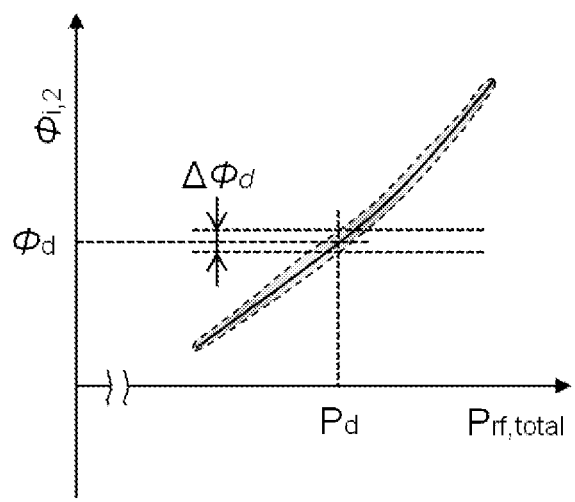
FIG. 8 is a graph for explaining design allowable bounds and a design phase characteristic required for the charged particle beam to be injected into the second-stage linear accelerator of the radio frequency accelerator according to Embodiment 1 of the present invention.

Next, the phase of the charged particles is considered. In order for the charged particles injected into the second-stage linear accelerator 3 to be accelerated, the charged particles need to have a suitable radio frequency phase $\phi_{i,2}$ when they are at the inlet of the second-stage linear accelerator 3. The suitable phase has a characteristic as shown in FIG. 8, taking the total radio frequency power $P_{rf,total}$ as the horizontal axis. In FIG. 8, the solid line indicates the center phase of the charged particle beam suitable for acceleration, and the two broken lines indicate limits of acceleration allowable bounds around the solid line, i.e., limits of the phase acceptance. The center phase and the phase acceptance can be calculated by computer analysis, i.e., by design. The bounds of the phase acceptance for a certain value of the phase $\phi_d$ is a range of $\Delta\phi_d$ as shown in FIG. 8. It is found from the phase acceptance characteristic that a radio frequency power range in which the charged particle beam having a certain value of the phase $\phi_d$ can be accelerated by the second-stage linear accelerator 3, i.e., an allowable range is $\Delta P_b$ shown in FIG. 9. Conventionally, a radio frequency power range possible for the acceleration has been considered to be the range $\Delta P_b$ only. However, it is proved by the following analysis of the present inventors that there exists a condition that allows for acceleration in the second-stage linear accelerator 3 over a radio frequency power range wider than $\Delta P_b$.

Let $v_{o,1}$ be the velocity of the charged particles at the time when they are at the outlet of the first-stage linear accelerator 2, and $\phi_{o,1}$ be the phase at the outlet of the first-stage linear accelerator 2 of the charged particles extracted from the first-stage linear accelerator 2, i.e., the phase of the radio frequency wave at that time. The charged particle velocity $v_{o,1}$ can be easily converted from $E_{o,1}$. Letting L be the length of the matching section, i.e., the distance from the outlet of the first-stage linear accelerator 2 to the inlet of the second-stage linear accelerator 3 and $\omega$ be the angular frequency of the radio frequency wave, the phase of the radio frequency wave advances by $L/(\omega^* v_{o,1})$ while the charged particles travel in the matching section. Accordingly, when the charged particles that have the phase $\phi_{o,1}$ at the outlet of the first-stage linear accelerator 2 reach the inlet of the second-stage linear accelerator 3, the phase of the radio frequency wave is expressed below:

$$\phi_{o,1} + L/(\omega^* v_{o,1}) \qquad (1).$$

Figure 10:
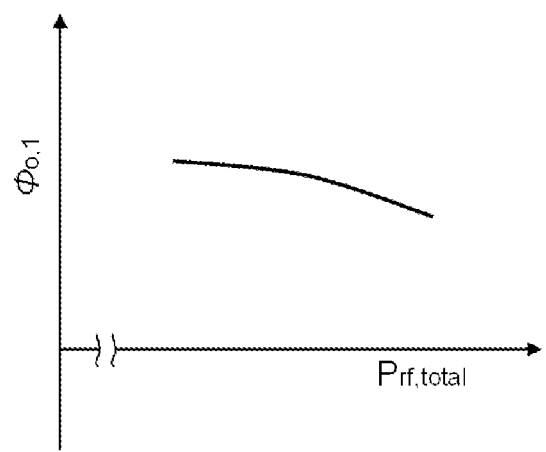
FIG. 10 is a graph showing an example of a phase characteristic of the charged particle beam extracted from the first-stage linear accelerator of the radio frequency accelerator according to Embodiment 1 of the present invention.
Figure 11:
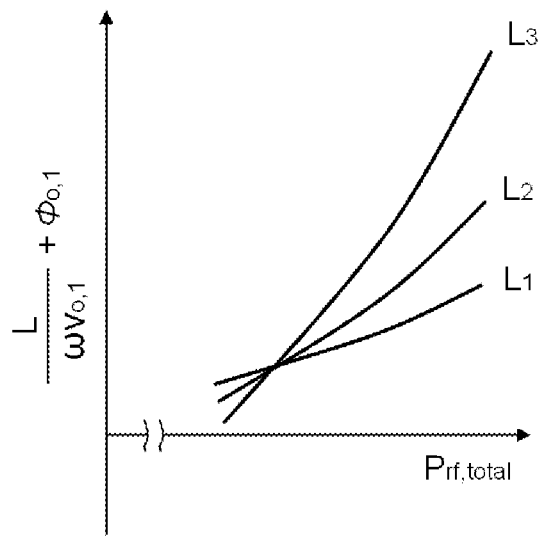
FIG. 11 is a graph showing an example of phase characteristics of the charged particle beam when it reaches the inlet of the second-stage linear accelerator from the first-stage linear accelerator, in the radio frequency accelerator according to Embodiment 1 of the present invention.

The phase $\phi_{o,1}$ of the charged particles at the outlet of the first-stage linear accelerator 2 does not largely vary with respect to the radio frequency power as shown in FIG. 10. The charged particle Energy E is proportional to the square of the charged particle velocity v if the velocity is not a relativistic velocity. Considering the characteristics shown in FIG. 10 and FIGS. 3 and 5, the phases of the charged particle beam when it reaches the inlet of the second-stage linear accelerator 3 from the first-stage linear accelerator 2, i.e., values of the expression (1) are as shown in FIG. 11, taking as the horizontal axis the total radio frequency power $P_{rf,total}$ supplied from the radio frequency power source. FIG. 11 shows values of the expression (1) with three values of the matching section length L ($L_1 < L_2 < L_3$) being taken as parameters. Since the phase varies largely with increasing L, the slopes become larger. Note that while the actual parameter is $L/\omega$ as seen from the expression (1), $\omega$ is assumed constant in the above explanation.

Figure 9:
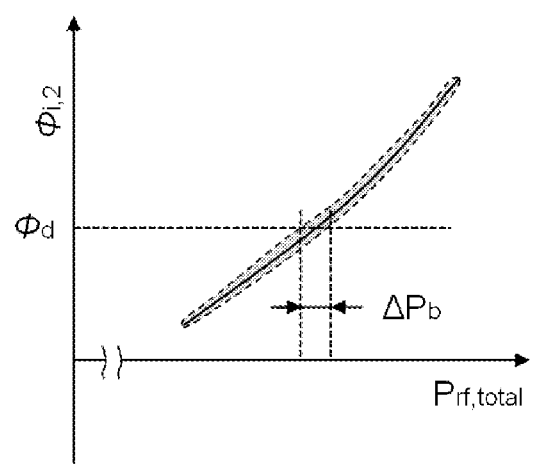
FIG. 9 is another graph for explaining the design allowable bounds and the design phase characteristic required for the charged particle beam to be injected into the second-stage linear accelerator of the radio frequency accelerator according to Embodiment 1 of the present invention.
Figure 12:
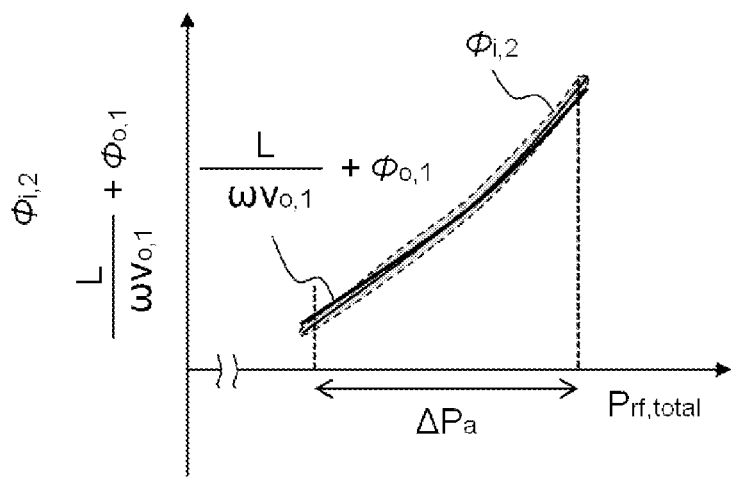
FIG. 12 is a graph for explaining matching of a phase characteristic of the charged particle beam when it reaches the inlet of the second-stage linear accelerator from the first-stage linear accelerator with a design phase characteristic required for the charged particle beam to be injected into the second-stage linear accelerator, in the radio frequency accelerator according to Embodiment 1 of the present invention.

Thus, preferably selecting a values of L that causes a portion of a characteristic falling within phase acceptance bounds shown in FIG. 9 to be the maximum among those of characteristics with values of L being taken as parameters as shown in FIG. 11, permits the charged particles to be accelerated by the second-stage linear accelerator 3 even when the output power of the radio frequency power source is varied widely. Such a preferable situation is shown in FIG. 12. Similarly to FIGS. 8 and 9, FIG. 12 schematically shows a center phase $\phi_{i,2}$ (the fine solid line) and phase acceptance bounds (indicated by the bounds between the broken lines) of the charged particle beam that can be accelerated by the second-stage linear accelerator 3, and a characteristic (the bold solid line) in the case of a value of L that causes a portion of the characteristic falling within the phase acceptance bounds to be the maximum among those of characteristics of the expression (1). In the case of the characteristic shown in FIG. 12, the charged particles can be accelerated by the first- and the second-stage linear accelerators over the radio frequency power range $\Delta P_a$, thus enabling a charged particle beam to be extracted from the second-stage linear accelerator 3. As described above, it is elucidated that the radio frequency accelerator 10 is obtained that is configured with the combination of a RFQ linac as the first-stage linear accelerator 2 and an AFP-IH DTL as the second-stage linear accelerator 3, and is capable of extracting a charged particle beam over a wide range of radio frequency power by setting properly the length of the matching section 8.

In addition, if the center value of the phase of the charged particle beam when it reaches the inlet of the second-stage linear accelerator 3 from the first-stage linear accelerator 2 is coincide with the center value of the phase acceptance of the second-stage linear accelerator 3 and if the phase spread of the charged particle beam extracted from the first-stage linear accelerator 2 is within the phase acceptance, the transmission efficiency is 100%. Deviation of the center value of the phase of the charged particle beam at the inlet of the second-stage linear accelerator 3 reduces the transmission efficiency even when the phase spread is within the phase acceptance. Further deviation of the center value of the phase of the charged particle beam at the inlet of the second-stage linear accelerator 3 from the phase acceptance will reduces the transmission efficiency to 0% irrespective of the phase spread. In particular, since an APF-IH DTL has a narrow phase acceptance, the center value of the phase of the charged particle beam when it reaches the second-stage linear accelerator 3 from the first-stage linear accelerator 2 needs to be close to the center value of the phase acceptance of the second-stage linear accelerator 3.

The radio frequency accelerator 10 according to Embodiment 1 of the present invention is the combination of the first-stage linear accelerator 2 that is a RFQ linac and the second-stage linear accelerator 3 that is an APF-IH DTL, and is configured such that a radio frequency wave from one radio frequency power source is distributively supplied to the first-stage linear accelerator 2 and the second-stage linear accelerator 3 by the power distributor to accelerate charged particles. For the radio frequency accelerator thus configured, it is elucidated that the radio frequency accelerator can be provided that is capable of extracting a large-current charged particle beam over a wide radio frequency power range by properly setting the power distribution factor R of the power distributor and the length L of the matching section 8 between the first-stage linear accelerator and the second-stage linear accelerator. Note that the first-stage linear accelerator is not limited to a RFQ type but may be a radio frequency focused interdigital (RFI) type, and the second-stage linear accelerator is not limited to an APF type but may be an ordinary DTL.

Employing such linear accelerators also exhibits characteristics similar to those described above.

Figure 13:
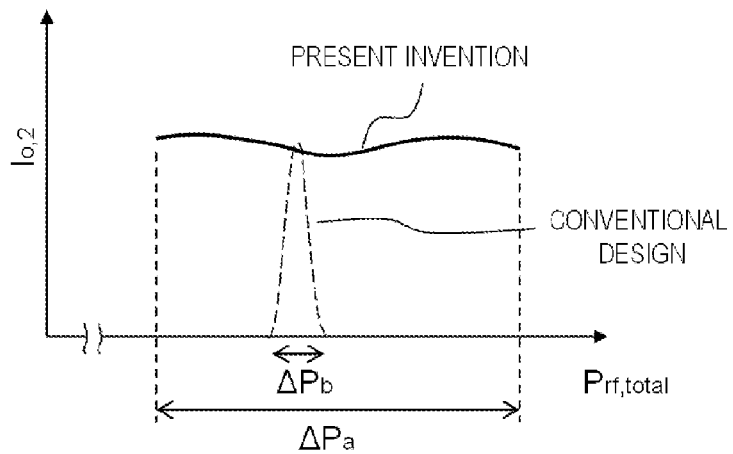
FIG. 13 is a graph showing operational characteristics of the radio frequency accelerator according to Embodiment 1 of the present invention, along with operational characteristics of a conventional radio frequency accelerator as a comparative example.

An example of output characteristics of the radio frequency accelerator 10 according to Embodiment 1 of the present invention is shown in FIG. 13. FIG. 13 shows a current value $I_{o,2}$ of the charged particle beam, which corresponds to the extracted amount of the charged particles extracted per unit time from the second-stage linear accelerator 3, taking as the horizontal axis the total radio frequency power $P_{rf,total}$ supplied from the radio frequency power source. The solid line indicates a characteristic example of $I_{o,2}$ extracted from the radio frequency accelerator 10 according to Embodiment 1 of the present invention, and the broken line indicates a characteristic example of $I_{o,2}$ obtained by a conventional design. Conventionally, since proper acceleration is achieved only in a narrow range of the total radio frequency power, i.e., only in the extent of allowable range $\Delta P_b$ of a second-stage linear accelerator as shown by the broken lines in FIG. 9, it has been considered that output of the accelerator is difficult to obtain by varying the value of the radio frequency power over a wide range. However, it is found that according to the present invention, output of the accelerator can be obtained even when the value of the total radio frequency power is varied over the wide range $\Delta P_a$ as indicated by the solid line in FIG. 13.

As described above, it is elucidated by the present inventors that a radio frequency accelerator can be obtained that is capable of accelerating charged particles over a wide radio frequency power range $\Delta P_a$ and of reducing current variation of the extracted charged particle beam even when the radio frequency power is varied, by setting properly the distribution factor of the radio frequency power for the two accelerator and the length of the matching section therebetween. While the allowable range $\Delta P_b$ shown in FIG. 9, of the total radio frequency power $P_{rf,total}$ for the charged particles having a phase to be injected into the second-stage linear accelerator varies with the value of the phase $\phi_d$, it is proved that there exists a condition that allows for acceleration in the second-stage linear accelerator 3 over a range wider than the widest range of $\Delta P_b$.

Figure 14:
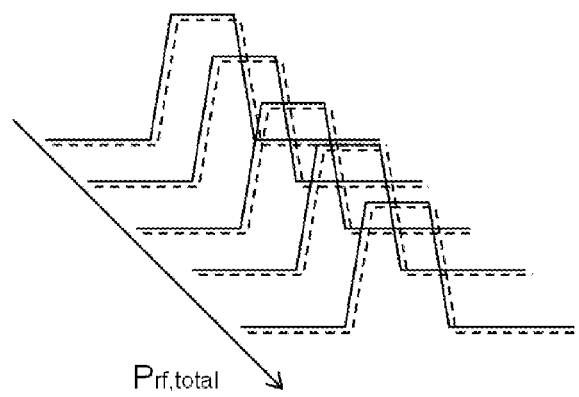
FIG. 14 is a conceptual graph for explaining operation of the radio frequency accelerator according to Embodiment 1 of the present invention.
Figure 15:
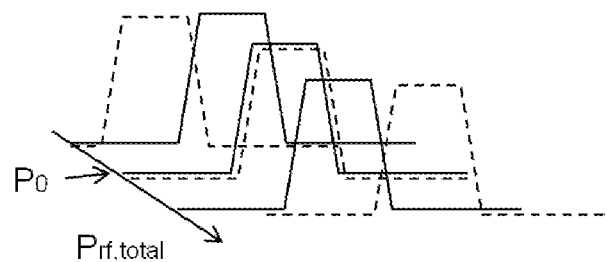
FIG. 15 is a conceptual graph for explaining operation of the conventional radio frequency accelerator.

The above-described operation of the radio frequency accelerator of the present invention and operation of a conventionally designed radio frequency accelerator are explained with reference to a conceptual figure. FIG. 14 is a conceptual graph for explaining operation of the radio frequency accelerator of the present invention, and FIG. 15 is a conceptual graph for explaining operation of the conventionally designed radio frequency accelerator. In FIGS. 14 and 15, the horizontal direction represents the phase of the charged particles and the arrow direction represents the total radio frequency power $P_{rf,total}$; and the solid lines indicate phase distributions of the charged particles extracted from the first-stage linear accelerator and the broken lines indicate phase acceptance of the second-stage linear accelerator. According to the present invention, since variation of the phase distribution of the charged particles extracted from the first-stage linear accelerator keeps up with variation of the phase acceptance of the second-stage linear accelerator as shown in FIG. 14 when the total radio frequency power is varied, the phase distribution of the charged particles extracted from the first-stage linear accelerator matches with the phase acceptance of the second-stage linear accelerator over a wide range of the total radio frequency power.

In the conventional design, on the other hand, when the phase distribution of the charged particle extracted from the first-stage linear accelerator and the phase acceptance of the second-stage linear accelerator are designed to match with each other at a certain value $P_0$ of the total radio frequency power, the both readily become out of matching as the total radio frequency power deviates from $P_0$, as shown in FIG. 15. Accordingly, the charged particles extracted from the first-stage linear accelerator cannot be accelerated by the second-stage linear accelerator only in a narrow range around $P_0$ of the total radio frequency power.

As described above, it is found from the present invention that the value of the power distribution factor R for the power distributor 7 to supply the radio frequency power to the second-stage linear accelerator 3 and the value of the ratio L/ω of the length L of the matching section 8 between the outlet of the first-stage linear accelerator 2 and the inlet of the second-stage linear accelerator 3 to the angular frequency ω of the radio frequency power, can be adjusted or set so that the charged particle beam is extracted from the second-stage linear accelerator over a wider range of $P_{rf,total}$ than the widest allowable range (which means a widest range among each $\Delta P_b$ determined for various values of $\phi_d$ by varying the value of $\phi_d$ as shown in FIG. 9) among the allowable ranges of the total radio frequency power determined for each phase of charged particles on the basis of phase acceptance of the second-stage accelerator. To what extent the radio frequency power range is wide for the charged particle beam to be extracted depends on the configuration and the like of the first-stage linear accelerator and the second-stage linear accelerator. Furthermore, it is found that the charged particle beam can be extracted over a range at least two times wider or more than the widest allowable range among allowable ranges of the total radio frequency power determined for each phase of charged particles on the basis of phase acceptance of the second-stage accelerator.

Figure 16:
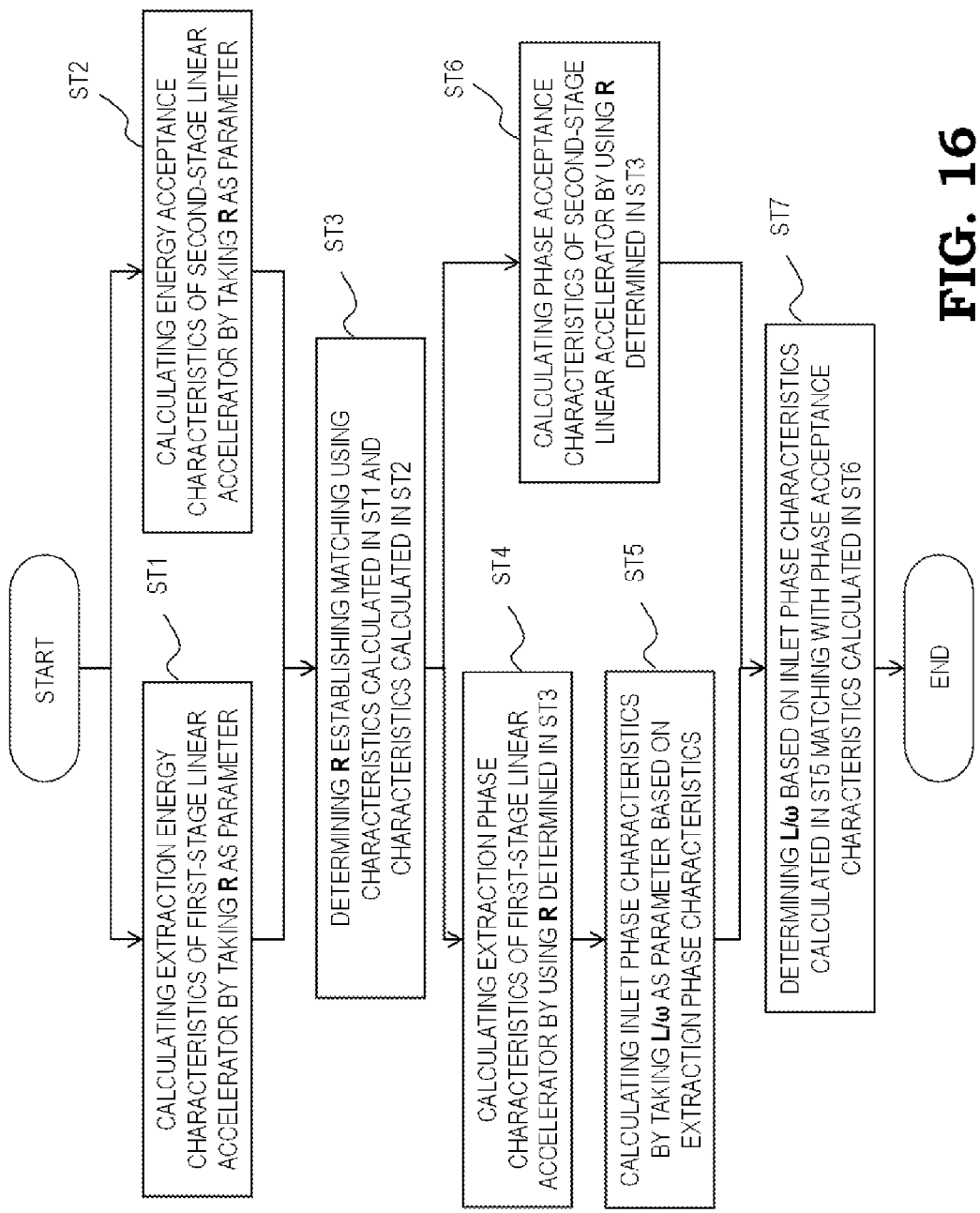
FIG. 16 is a flow diagram showing a process of manufacturing the radio frequency accelerator according to Embodiment 1 of the present invention.

FIG. 16 shows a flow diagram summarizing the above-described process of designing the radio frequency accelerator 10 according to Embodiment 1 of the present invention. First, extraction energy characteristics as shown in FIG. 5, of the charged particle beam extracted from the first-stage linear accelerator 2 are calculated to the radio frequency power $P_{rf,total}$ generated by the radio frequency power source, taking values of the power distribution factor R of the power distributor 7 as parameters (ST1). Parallel to the step ST1, energy acceptance characteristics as shown in FIG. 6 for the energy $E_{i,2}$ of the charged particle beam to be injected into the second-stage linear accelerator 3 are calculated to $P_{rf,total}$, taking values of the power distribution factor R as parameters (ST2). Next, among the extraction energy characteristics calculated in the step ST1, a characteristic calculated in the step ST2 that has a portion falling as much as possible within bounds of the energy acceptance characteristics, i.e., a value of the distribution factor R that establishes matching is determined (ST3).

Next, using the power distribution factor R determined in the step ST3, an extraction phase characteristic as shown in FIG. 10, which is a characteristic of the center phase $\phi_{o,1}(P_{rf,total})$ at the outlet of the first-stage linear accelerator 2, of the charged particle beam extracted from the first-stage linear accelerator 2, is calculated to $P_{rf,total}$ (ST4). Next, using the extraction phase characteristic, inlet phase characteristics as shown in FIG. 11, which are the characteristics of the center phase $\phi_{o,1}(P_{rf,total})+(L/\omega)/v(P_{rf,total})$ of the charged particle beam when it reaches the inlet of the second-stage linear accelerator 3 from the first-stage linear accelerator 2, are calculated taking values of L/ω as parameters (ST5).

Then, using the value of the power distribution factor R determined in the step ST3, a phase acceptance characteristic for the charged particle beam to be injected into the second-stage linear accelerator 3 is calculated to $P_{rf,total}$ (ST6). Next, among the inlet phase characteristics calculated in the step ST5 taking values of $L/\omega$ as parameters, a value of $L/\omega$ is determined on the basis of an inlet phase characteristic that matches with the phase acceptance characteristic calculated in the step ST6 (ST7). To be more specific, among the inlet phase characteristics calculated in the step ST5 taking values of $L/\omega$ as parameters, a value of $L/\omega$ is determined on the basis of an inlet phase characteristic falling within the bounds of the phase acceptance characteristics calculated in the step ST6 over a range of the total radio frequency power wider, at least two times wider or more than the widest allowable range among the allowable ranges of the total radio frequency power determined for each phase of charged particles on the basis of phase acceptance characteristics of the second-stage accelerator.

The design and the adjustment including the above process allows for manufacturing a radio frequency accelerator that ensures matching between the first-stage accelerator and the second-stage accelerator even when the supplied radio frequency power is varied in a range wider than the widest allowable range among the allowable ranges of the total radio frequency power determined for each phase of charged particles on the basis of phase acceptance characteristics of the second-stage accelerator, as explained in FIG. 9, and is easy to adjust the power. Moreover, in a case of employing the radio frequency accelerator as an injector for a circular accelerator as will be described in Embodiment 2, the radio frequency accelerator can generate by adjusting the radio frequency power a preferable characteristic of the charged particle beam to be injected into the circular accelerator.

Embodiment 2

Figure 17:
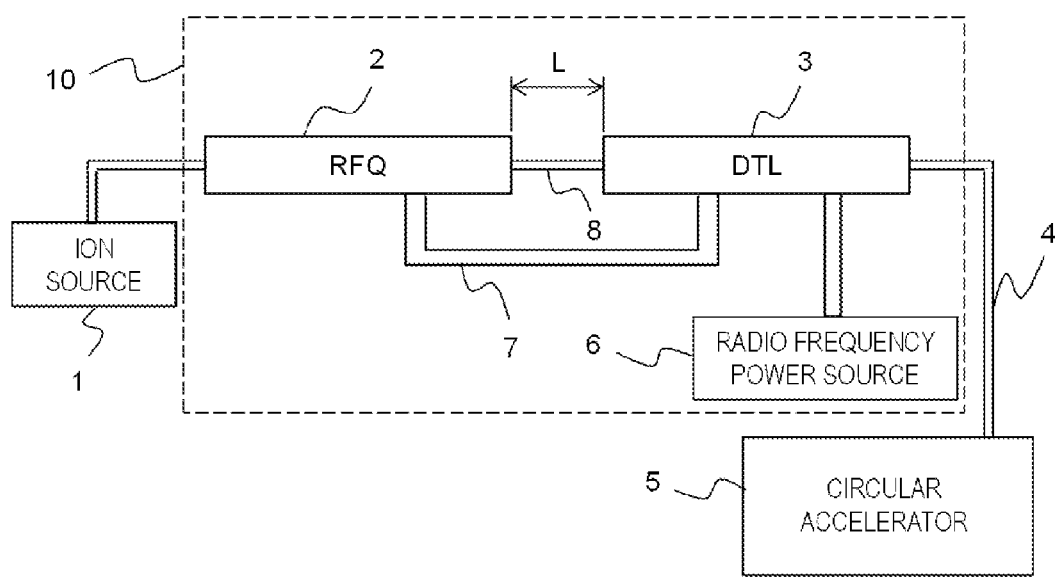
FIG. 17 is a block diagram schematically showing an overall configuration of a circular accelerator system including the radio frequency accelerator, according to Embodiment 2 of the present invention.

FIG. 17 is a block diagram schematically showing a configuration of a circular accelerator system according to Embodiment 2 of the present invention. A radio frequency accelerator 10 shown in FIG. 17 is the radio frequency accelerator described in Embodiment 1. The circular accelerator system according to Embodiment 2 is a system for accelerating the charged particle beam injected into a circular accelerator 5 such as a synchrotron from the radio frequency accelerator 10, to extract a charged particle beam having an energy level sufficient for a particle beam therapy system or the like to utilize the beam for irradiation of an irradiation target.

In a case of using a conventional radio frequency accelerator, a charged particle beam needs to be injected into a synchrotron through a device called a debuncher, which aligns the energy of and spreads the phase width of the charged particles in the charged particle beam. Using the radio frequency accelerator 10 according to Embodiment 1 of the present invention, however, the extracted charged particle beam is injected into the circular accelerator 5 not through a device such as the debuncher for adjusting a relationship between spread of the energy and spread of the phase but through a beam delivery system 4 configured with devices whose physical quantities acting on the charged particle beam are magnetic fields only, such as a bending magnet for bending the traveling direction of the beam, a quadrupole electromagnet for controlling transverse spread of the beam, and a steering electromagnet for correcting the beam path.

Figure 18A:
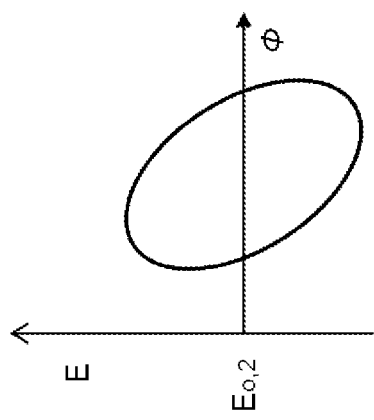
FIG. 18A through FIG. 18C are conceptual graphs expressing, in the phase-vs-energy space, characteristics of the charged particle beam output from the radio frequency accelerator according to Embodiment 1 of the present invention.
Figure 18B:
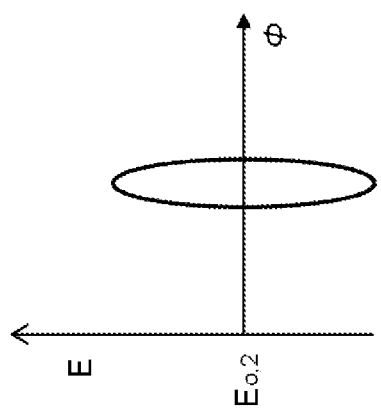
Figure 18C:
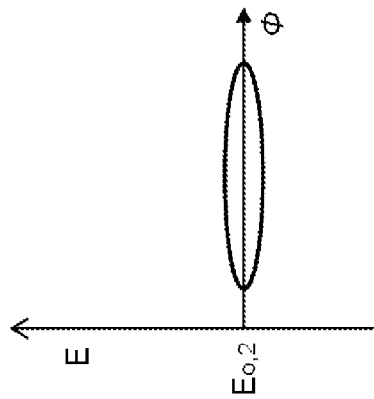

It has been described that the radio frequency accelerator 10 according to Embodiment 1 exhibits output characteristics with respect to the radio frequency power as indicated by the solid line in FIG. 13. Changing the radio frequency power does not largely vary the current value of the extracted charged particle beam but vary quality of the extracted charged particle beam. The quality variation is shown in FIG. 18A through FIG. 18C for explanation. FIG. 18A through FIG. 18C are conceptual graphs expressing distributions of the charged particles contained in the extracted charged particle beam in the phase $\phi$-vs-energy E space. Individual charged particles in the extracted charged particle beams accelerated by different radio frequency power $P_{rf,total}$ are distributed in the ellipses as shown in the respective graphs FIGS. 18A, 18B and 18C. As shown in the figures, when the radio frequency power is varied, the extracted charged particle beam exhibits a characteristic such that the ellipse rotates with its area varying in the $\phi$-E space.

Figure 19:
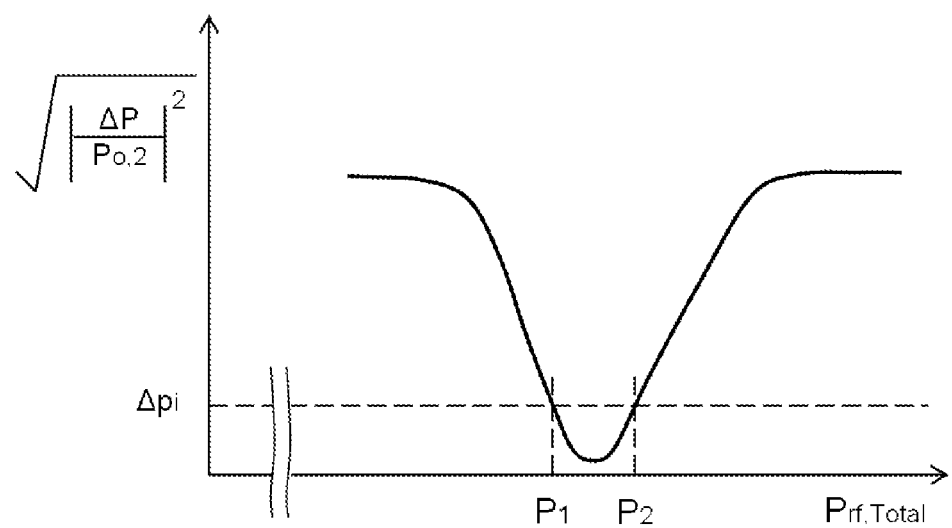
FIG. 19 is a graph showing a characteristic of the energy width of the charged particle beam output from the radio frequency accelerator according to Embodiment 1 of the present invention.

FIG. 19 is a graph showing a distribution of the charged particles varying as shown in FIG. 18 through FIG. 18C. The distribution is expressed as a characteristic of momentum spread width $\sqrt{|\Delta P/P_{o,2}|^2}$ (also referred to as "momentum spectrum"), which corresponds to energy width, with respect to the radio frequency power $P_{rf,total}$. The momentum spectrum width varies in response to variation of the radio frequency power as shown in FIG. 19.

In order to accelerate charged particles by the circular accelerator 5 such as a synchrotron, a charged particle beam having a desired narrow momentum spectrum needs to be injected thereinto. For example, assuming a momentum spectrum suitable for acceleration by the circular accelerator 5 to be $\Delta p_i$ shown in FIG. 19, a charged particle beam having the momentum spectrum suitable for the acceleration by the circular accelerator 5 can be extracted by setting, as shown in FIG. 19, to $P_1$ or $P_2$ the radio frequency power of the radio frequency accelerator 10 according to Embodiment 1 of the present invention. As a result, while a device such as a debuncher for adjusting the relationship between energy spread and phase spread is necessary in using a conventional radio frequency accelerator, employing the radio frequency accelerator 10 according to Embodiment 1 of the present invention provides a circular accelerator system that is capable of accelerating efficiently by the circular accelerator 5 a charged particle beam extracted from the radio frequency linear accelerator 10 without the need of such a device for adjusting the relationship between energy spread and phase spread.

Each embodiment of the present invention may appropriately modified or omitted within the spirit and scope of the present invention.

REFERENCE NUMERALS

1: ion source;
2: first-stage linear accelerator;
3: second-stage linear accelerator;
4: beam delivery system;
5: circular accelerator;
6: radio frequency power source;
7: resonant-coupler-type power distributor;
8: matching section;
10: radio frequency accelerator.

The invention claimed is:
1. A method of manufacturing a radio frequency accelerator that includes a first-stage linear accelerator for accelerating charged particles injected into the first-stage linear accelerator from an ion source; a second-stage linear accelerator for accelerating a charged particle beam injected into the second-stage linear accelerator from the first-stage linear accelerator through a matching section; a radio frequency power source for generating total radio frequency power to be supplied to the first-stage linear accelerator and the second-stage linear accelerator; and a power distributor for distributively supplying the total radio frequency power supplied from the radio frequency power source to the first-stage linear accelerator and the second-stage linear accelerator, the method of manufacturing the radio frequency accelerator including:
- a step of setting a value of a power distribution factor R for the power distributor to supply the radio frequency power to the second-stage linear accelerator and a value of a ratio $L/\omega$ of a length L of the matching section between an outlet of the first-stage linear accelerator and an inlet of the second-stage linear accelerator to an angular frequency $\omega$ of the radio frequency power, so that a charged particle beam is extracted from the second-stage linear accelerator over a range of the total radio frequency power wider than a widest allowable range among allowable total radio frequency power ranges determined for each phase of charged particles on the basis of phase acceptance of the second-stage accelerator.

2. The method of manufacturing the radio frequency accelerator, set forth in claim 1 further including:
- a first step of calculating, taking values of R as parameters, extraction energy characteristics, which are center-energy characteristics of the charged particle beam extracted from the first-stage linear accelerator, with respect to the total radio frequency power;
- a second step of calculating, taking values of R as parameters, energy acceptance characteristics for the charged particle beam to be injected into the second-stage linear accelerator with respect to the total radio frequency power;
- a third step of determining a value of R that matches an extraction energy characteristic calculated in the first step with an energy acceptance characteristic calculated in the second step;
- a fourth step of calculating, using the value of R determined in the third step, an extraction phase characteristic of the charged particle beam extracted from the first-stage linear accelerator, which is a characteristic of a center phase $\phi_{o,1}$ at an outlet of the first-stage linear accelerator, with respect to the total radio frequency power;
- a fifth step of calculating, letting v be a velocity of the charged particles in the charged particle beam extracted from the first-stage linear accelerator and using the extraction phase characteristic calculated in the fourth step, inlet phase characteristics, which are characteristics of a center phase $\phi_{o,1}+(L/\omega)/v$ of the charged particle beam when the charged particle beam reaches the second-stage linear accelerator from the first-stage linear accelerator, taking values of $L/\omega$ as parameters;
- a sixth step of calculating, using the value of R determined in the third step, a phase acceptance characteristic for the charged particle beam to be injected into the second-stage accelerator with respect to the total radio frequency power;
- a seventh step of determining a value of $L/\omega$ on the basis of an inlet phase characteristic, among the inlet phase characteristics calculated in the fifth step taking values of $L/\omega$ as parameters, falling within the phase acceptance characteristic calculated in the sixth step over a range of the total radio frequency power wider than a widest allowable range among the allowable total radio frequency power ranges determined for each phase of charged particles on the basis of phase acceptance of the second-stage accelerator; and
- an eighth step of setting the power distribution factor R of the power distributor to the value determined in the third step, and setting a length L of the matching section to the value determined in the seventh step.

3. The method of manufacturing the radio frequency accelerator, set forth in claim 2, wherein a value of $L/\omega$ is determined in the seventh step on the basis of the inlet phase characteristic, among the inlet phase characteristics calculated in the fifth step taking values of $L/\omega$ as parameters, falling within the phase acceptance characteristic calculated in the sixth step over a total radio frequency power range at least two times wider or more than the widest allowable ranges among the allowable total radio frequency power ranges determined for each phase of charged particles on the basis of phase acceptance of the second-stage accelerator.

4. The method of manufacturing the radio frequency accelerator, set forth in claim 1 further including a step of setting a value of the power distribution factor R for the power distributor to supply the radio frequency power to the second-stage linear accelerator and a value of the ratio $L/\omega$ of the matching section length L between the outlet of the first-stage linear accelerator and the inlet of the second-stage linear accelerator to the angular frequency $\omega$ of the radio frequency power, so that the charged particle beam is extracted from the second-stage linear accelerator over a total radio frequency power range two times wider or more than the widest allowable range among the allowable total radio frequency power ranges determined for each phase of charged particles on the basis of phase acceptance of the second-stage accelerator.

5. The method of manufacturing the radio frequency accelerator, set forth in claim 1, wherein the first-stage linear accelerator is a RFQ linac and the second-stage linear accelerator is an APF-IH DTL.

6. The method of manufacturing the radio frequency accelerator, set forth in claim 1, wherein the power distributor is a resonant-coupler-type power distributor.

7. A radio frequency accelerator comprising:
- a first-stage linear accelerator for accelerating charged particles injected into the first-stage linear accelerator from an ion source to extract the accelerated charged particles as a charged particle beam;
- a second-stage linear accelerator for accelerating the charged particle beam injected into the second-stage linear accelerator from the first-stage linear accelerator through a matching section to extract the accelerated charged particle beam;
- a radio frequency power source for generating total radio frequency power to be supplied to the first-stage linear accelerator and the second-stage linear accelerator; and
- a power distributor for distributively supplying the total radio frequency power supplied from the radio frequency power source to the first-stage linear accelerator and the second-stage linear accelerator, wherein a value of a power distribution factor R for the power distributor to supply the radio frequency power to the second-stage linear accelerator and a value of a ratio $L/\omega$ of a length L of the matching section between an outlet of the first-stage linear accelerator and an inlet of the second-stage linear accelerator to an angular frequency $\omega$ of the radio frequency power are set so that the charged particle beam is extracted from the second-stage linear accelerator over a range of the total radio frequency power wider than a widest allowable range among allowable total radio frequency power ranges determined for each phase of charged particles on the basis of phase acceptance of the second-stage accelerator.

8. The radio frequency accelerator set forth in claim 7, wherein a value of the power distribution factor R for the power distributor to supply the radio frequency power to the second-stage linear accelerator and a value of the ratio $L/\omega$ of the matching section length L between the outlet of the first-stage linear accelerator and the inlet of the second-stage linear accelerator to the angular frequency ω of the radio frequency power are set so that the charged particle beam is extracted from the second-stage linear accelerator over a total radio frequency power range two times wider or more than the widest allowable range among the allowable total radio frequency power ranges determined for each phase of charged particles on the basis of phase acceptance of the second-stage accelerator.

9. The radio frequency accelerator set forth in claim 7, wherein the first-stage linear accelerator is a RFQ linac and the second-stage linear accelerator is an APF-IH DTL.

10. The radio frequency accelerator set forth in claim 7, wherein the power distributor is a resonant-coupler-type power distributor.

11. A circular accelerator system comprising:
a radio frequency accelerator set forth in claim 7;
a beam delivery system for delivering a charged particle beam extracted from the radio frequency accelerator;
a circular accelerator for accelerating the charged particle beam delivered by the beam delivery system and injected into the circular accelerator, wherein
physical quantities acting on the charged particle beam in the beam delivery system are magnetic fields only.

12. The circular accelerator system set forth in claim 11, wherein radio frequency power of the radio frequency power source is set so that the charged particle beam to be injected into the circular accelerator has an energy width equal to a design energy width for the charged particle beam to be injected into the circular accelerator.

* * * * *